(12) United States Patent
O'Clock

(10) Patent No.: US 11,007,367 B2
(45) Date of Patent: May 18, 2021

(54) MICROCURRENT DEVICE FOR THE TREATMENT OF VISUAL DISEASE

(71) Applicant: NOVA OCULUS CANADA MANUFACTURING ULC, Fergus (CA)

(72) Inventor: George D. O'Clock, Waconia, MN (US)

(73) Assignee: NOVA OCULUS CANADA MANUFACTURING ULC, Fergus (CA)

(*) Notice: Subject to any disclaimer, the term of this patent is extended or adjusted under 35 U.S.C. 154(b) by 0 days.

(21) Appl. No.: 15/071,912

(22) Filed: Mar. 16, 2016

(65) Prior Publication Data

US 2017/0266445 A1    Sep. 21, 2017

(51) Int. Cl.
*A61N 1/36* (2006.01)
*A61N 1/04* (2006.01)

(52) U.S. Cl.
CPC ..... *A61N 1/36046* (2013.01); *A61N 1/36014* (2013.01); *A61N 1/36034* (2017.08); *A61N 1/0408* (2013.01)

(58) Field of Classification Search
None
See application file for complete search history.

(56) References Cited

U.S. PATENT DOCUMENTS

| 4,989,605 A | 2/1991 | Rossen |
| 5,395,398 A | 3/1995 | Rogozinski |
| 5,522,864 A | 6/1996 | Wallace et al. |
| 6,035,236 A | 3/2000 | Jarding et al. |
| 6,275,735 B1 | 8/2001 | Jarding et al. |
| 7,251,528 B2 | 7/2007 | Harold |
| 8,612,008 B2 | 12/2013 | Kirsch et al. |
| 2003/0233137 A1 | 12/2003 | Paul |
| 2004/0176820 A1 | 9/2004 | Paul |

(Continued)

FOREIGN PATENT DOCUMENTS

| EP | 2694156 A2 | 2/2014 |
| JP | 2005-102949 | 4/2005 |

(Continued)

OTHER PUBLICATIONS

O'Clock, G.D., Book, "Electrotherapeutic Devices: Principles, Design and Applications", Artech House Pub., Boston, MA (2007), the entire book is being submitted.

(Continued)

*Primary Examiner* — Michael W Kahelin
*Assistant Examiner* — Elizabeth K So
(74) *Attorney, Agent, or Firm* — Stinson LLP

(57) ABSTRACT

An electrotherapeutic device for treating a visual disease using microcurrent stimulation is provided. The device includes a signal generator in which a waveform controller digitally controls a waveform signal source so as to generate a waveform in which one or more waveform parameters (e.g., pulse width, pulse period, pulse position, pulse coding, peak current amplitude, duty cycle, and/or pulse shape) are varied in accordance with a protocol for treating a visual disease. The device also includes an applicator connected to the signal generator and configured to apply the waveform to at least one stimulation point within an eye region.

21 Claims, 12 Drawing Sheets

(56) References Cited

U.S. PATENT DOCUMENTS

| | | |
|---|---|---|
| 2005/0004625 A1 | 1/2005 | Chow |
| 2008/0125832 A1* | 5/2008 | Horsager ............ A61N 1/36046 607/54 |
| 2013/0066396 A1 | 3/2013 | Gekeler |
| 2014/0257428 A1* | 9/2014 | Zhu .................... A61N 1/36178 607/46 |
| 2015/0018927 A1 | 1/2015 | Warschewske |
| 2015/0032170 A1 | 1/2015 | Gilman et al. |

FOREIGN PATENT DOCUMENTS

| | | |
|---|---|---|
| JP | 2005-529689 | 10/2005 |
| JP | 2014-514070 | 6/2014 |
| WO | WO 2000/002622 A1 | 1/2000 |
| WO | WO 2008/145724 A1 | 12/2008 |
| WO | WO 2017/048731 A1 | 3/2017 |

OTHER PUBLICATIONS

Yue, Lan, et al., "Retinal Stimulation Strategies to Restore Vision: Fundamentals and Systems", Progress in Retinal and Eye Research, vol. 53, pp. 21-47 (2016) (27 pgs).

Anastassiou, G., Article, "Transpalpebral electrotherapy for dry age-related macular degeneration (AMD): An exploratory trial", Restorative Neurology and Neuroscience, vol. 31 (2013) pp. 571-578 (9 pgs).

Shinoda, K., Article, "Transcutaneous Electrical Retinal Stimulation Therapy for Age-Related Macular Degeneration", The Open Ophthalmology Journal, vol. 2, (2008) pp. 132-136 (5 pgs).

Dor, H, Article, "Beitrage zur Electrotherapie der Augenkrankheiten" (Translation: "Contributions for Electrotherapy of Eye Diseases"), Albrecht von Graefes Archiv fur Opthalmologie, vol. 19 (1873) pp. 316-352 (37 pgs) (This reference is written in German).

Derby, H., Article, "On the Possible Retardation of Retinitis Pigmentosa", Trans Am Ophthalmol Soc., vol. 4 (1886) pp. 217-227 (11 pgs).

O'Clock, G.D., et al., Article, "Electrotherapeutic Device/Protocol Design Considerations for Visual Disease Applications," Proceedings of the 31st Annual International IEEE Engineering in Medicine and Biology Society Conference (EMBC '09), Sep. 2-6, 2009, Minneapolis, MN, pp. 2133-2136 ( 4 pgs).

International Search Report and Written Opinion dated May 24, 2017 from PCT/US2017/022416 (18 pgs).

McGehee, F, website blog, "How Does Microcurrent Therapy Work?", obtained from website "Wayback Machine" as visible on internet on Jul. 16, 2015, https://web.archive.org/web/20150716004702/http://www.machular-degeneration.net/about-microcurrent (2 pgs), downloaded from the internet on Oct. 13, 2016.

Kondrot, website blog, "Microcurrent Stimulation", obtained from website "Wayback Machine" as visible on internet on Mar. 31, 2015, https://web.archive.org/web/20150331174948/http://www.healingtheeye.com/microcurrent (4 pgs), downloaded from the internet on Oct. 13, 2016.

Grossman, M, website blog, "How Microcurrent Stimulation Could Help Eye Diseases", obtained from website "Wayback Machine" as visible on internet on Jun. 3, 2013, https://web.archive.org/web/20130603120513/http://www.naturaleyecare.com/blog/how-microcurrent-stimulation-help-eye-diseases (1 pg), downloaded from the internet on Oct. 13, 2016.

Ronald Trahn Associates, Inc., Press Release, "EBS Technologies Reports That a Clinical Study Published in Neurology Validates Electrical Brain Stimulation Technology Designed to Expand the Visual Field of Patients with Impaired Vision", published on the internet at http ://venturebeat.com/2014/09/18/3bs-technologies-reports-that-a-clinical-study-published-in-neurology-validates-electrical-brain-stimulation-technology-designed-to-expand-the-visual-field-of-patients-with-impaired-vision published Sep. 18, 2014 (3 pgs), downloaded from the internet on Oct. 13, 2016.

Jarding, J. et al, Chapter 47 entitled "Biocurrent Therapy for Macular Degeneration" published in book titled *Bioelectromagnetic Medicine,* published by Marcel Dekker, Inc., New York, NY (2004), 2 title pages and pp. 771-780 (12 pgs).

O'Clock, G.D., Book, "Electrotherapeutic Devices: Principles, Design and Applications", Artech House Pub., Boston, MA (2007), selected pages: Title page, Introduction, Table of Contents, pp. 1-9; 118-125; 128-133; 178-181; 196-199 (18 pgs).

Butterwick et al., "Tissue Damage by Pulsed Electrical Stimulation", IEE Transactions on Biomedical Engineering, vol. 54, No. 12, Dec. 2007 (8 pgs).

Cukjati et al., Chapter 31, "Electric Current Wound Healing", Bioelectromagnetic Medicine, P.J. Rosch and M. Markove, (eds), New York, Marcel Dekker, 2004, pp. 485-505 (21 pgs).

Zhao et al., "Electric Field-directed Cell Motility Involves Up-regulated Expression and Asymmetric Redistribution of the Epidermal Growth Factor Receptors and Is Enhanced by Fibronectin and Laminin", Molecular Biology of the Cell, vol. 10, pp. 1259-1276, Apr. 1999 (18 pgs).

Cheng et al., "The Effects of Electric Currents on ATP Generation, Protein Synthesis, and Membrane Transport in Rat Skin", Clinical Orthopedics and Related Research, vol. 171, pp. 264-271, 1982 (8 pgs).

Butterwick et al., "Dynamic Range of Safe Electrical Stimulation of the Retina", SPIE Proceedings, Ophthalmic Technologies XVI, SPIE vol. 6138 (2006) (8 pgs).

Michael et al., "Nutritional Supplementation, Electrical Stimulation and Age Related Macular Degeneration", Journal of Orthomolecular Medicine, vol. 8, No. 3, 1993 (4 pgs).

"Transcorneal Electrical Stimulation Therapy for Retinal Disease", downloaded on Dec. 7, 2017 from http://clinicaltrials.gov/ct2/show/record/NCT00804102 (7 pgs).

Allen, et al., "Macular Degeneration Treatment with Nutrients and Micro Current Electricity", Journal of Orthomolecular Medicine, vol. 13, No. 4, 1998 (4 pgs).

Humayn, et al., "Visual Perception Elicited by Electrical Stimulation of Retina in Blind Humans", Archives of Opthalmology, vol. 114, No. 1, Jan. 1996 (7 pgs).

\* cited by examiner

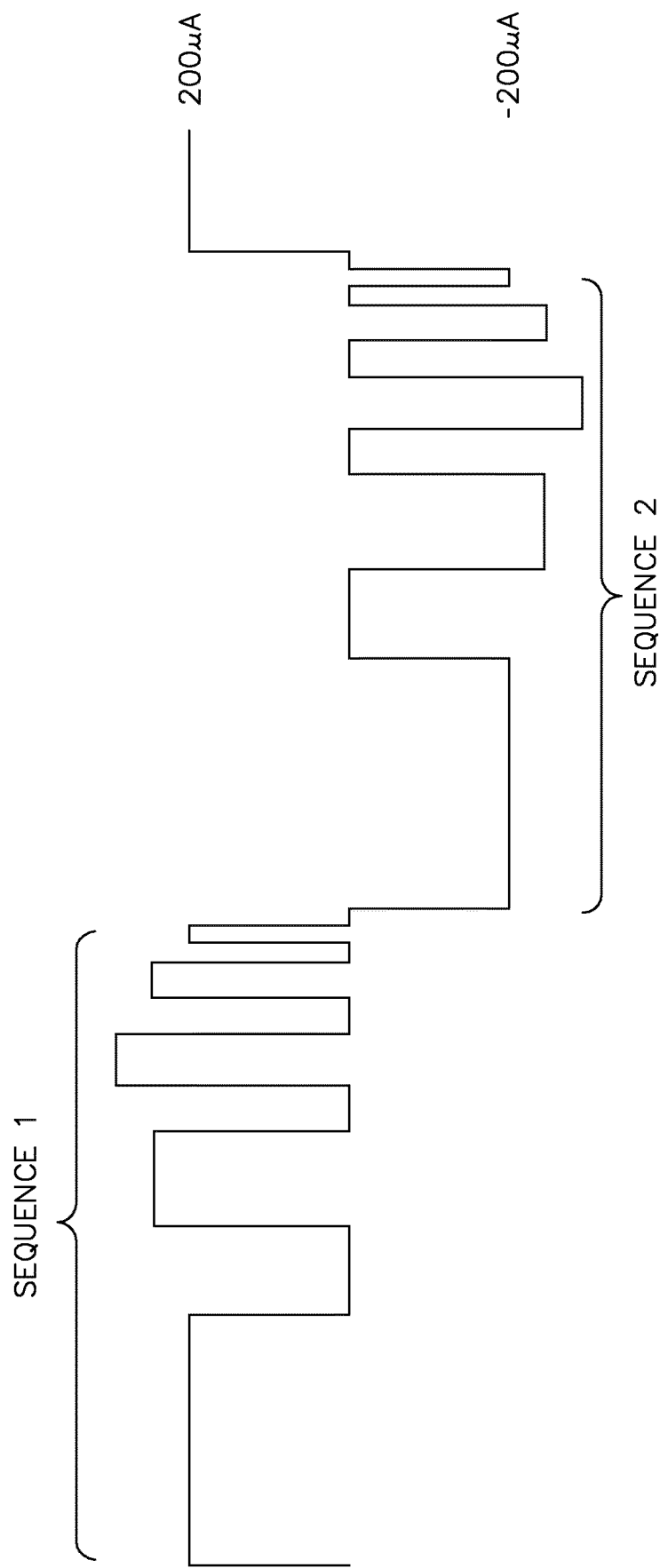

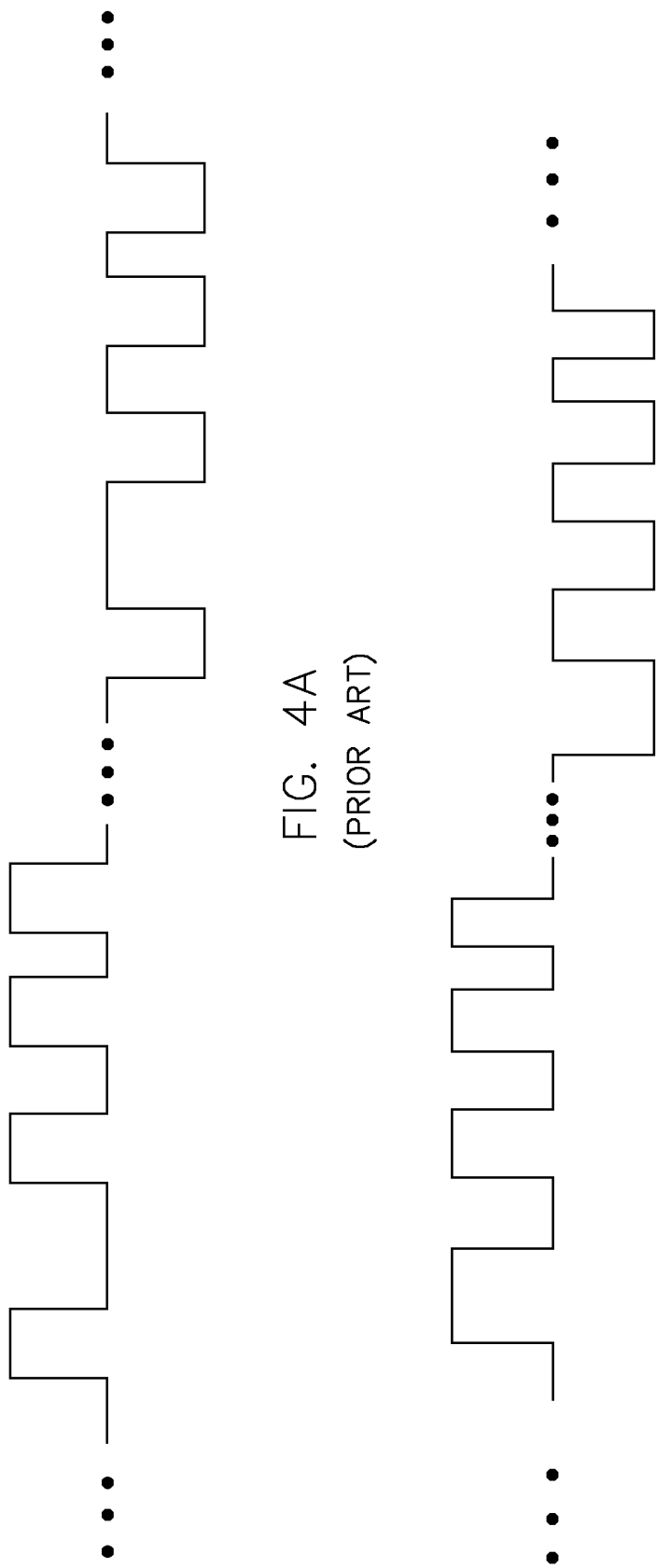

MICROCURRENT DEVICE FOR THE TREATMENT OF VISUAL DISEASE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates generally to devices and methods for electrical stimulation therapy, and more particularly to electrotherapeutic devices and methods that provide microcurrent stimulation to tissue of an eye region for the treatment of macular degeneration and other visual diseases.

2. Description of Related Art

Electrical stimulation therapy has emerged as a viable treatment modality for numerous diseases and disorders of the human body. One method of providing electrical stimulation therapy is to deliver microcurrent, which is typically defined as current below 1 milliamp, to tissue on or near the area of the body to be treated. For example, microcurrents in the range of 100 microamps to 1,000 microamps (peak) have been applied to tissue on or near a closed eyelid to treat macular degeneration and other visual diseases.

Normal retinal cell function involves a photochemical reaction that converts light energy to an electrical impulse, which travels from the optic nerve to the visual cortex (at the posterior end of the brain) that processes visual information. With macular degeneration and other visual diseases, diseased retinal cells eventually lose cell function such that adenosine triphosphate (ATP) levels decrease, protein synthesis and transport deteriorate, the cells become overwhelmed with an increase in toxicity, the cell membrane electrical potential decreases, and vascular blood flow is compromised. Basically, the retinal cells seem to go dormant for a period of time before they die. It is believed that, if microcurrent stimulation is provided to the retinal cells before cell death occurs, ATP levels increase, protein synthesis and transport are restored, the toxicity of the cells is mitigated, blood vessel permeability increases, a more normal cell membrane electrical potential is achieved, and normal cell metabolism is restored. In addition, it is believed that microcurrent stimulation has a healing effect on the small blood vessels in the retina, promoting a more efficient delivery of nutrients to the retinal cells and a more efficient uptake of proteins that can accumulate on the retina. Thus, microcurrent stimulation causes rejuvenation of the retinal cells to slow or stop degeneration of the eye due to macular degeneration and other visual diseases. In addition, animal studies indicate that microcurrent stimulation provided to the retinal cells provides a protective aspect for the retina with respect to being neuroprotective and photoreceptor protective, possibly due in part to the production/release of specific neurotrophic factors (which can include growth factors and cytokines).

Some of the earliest electrotherapeutic devices that provided electrical stimulation in visual disease applications were developed from the late 1700's to the late 1800's. These devices comprised stacks of wet cell batteries with electrodes connected to the battery electrodes that were used to treat neuropathy and retinitis pigmentosa with direct electric current (DC). A more recent patent that describes this type of electrotherapeutic device is U.S. Pat. No. 5,522,864 to Wallace, et al. and entitled "Apparatus and Method for Ocular Treatment," which discloses the use of a 200 microamp direct current generator to treat macular degeneration and other ocular pathology. These electrotherapeutic devices are very limited in scope with respect to output (i.e., only direct current) and capabilities.

Other electrotherapeutic devices that have been used to treat visual diseases are transcutaneous electrical nerve stimulation (TENS) devices. An example of a TENS device is described in U.S. Pat. No. 4,989,605 to Rossen and entitled "Transcutaueous Electrical Nerve Stimulation (TENS) Device," which discloses a device that generates a monophase DC carrier signal modulated using current levels of 25 microamps to 900 microamps for pain management. The Rossen device has been used in a number of studies to treat macular degeneration. See, e.g., G. D. O'Clock and J. B. Jarding, "Electrotherapeutic Device/Protocol Design Considerations for Visual Disease Applications," Proceedings of the 31st Annual International IEEE Engineering in Medicine and Biology Society Conference (EMBC '09), pp. 2133-2136, Sep. 2-6, 2009, Minneapolis, Minn. From the standpoint of clinical success and therapeutic efficacy in visual disease applications, the Rossen device has shown some positive results that are believed to be attributable to its DC offset and the lower frequency elements of its waveform.

Other TENS devices that followed the general design of the Rossen device include those described in U.S. Pat. No. 5,395,398 to Rogozinski and entitled "Microelectric Apparatus for the Antisepsis, Promulgation of Healing and Analgesia of Wound and Chronic Skin Ulcers," U.S. Patent Application Publication No. US2003/0233137 to Paul and entitled "Transcutaneous Electrical Nerve Stimulation Device and Method Using Microcurrent," and U.S. Pat. No. 7,251,528 to Harold and entitled "Treatment of Vision Disorders Using Electrical, Light, and/or Sound Energy."

One problem with TENS devices is that many of them utilize complex and overlapping waveforms that can be detrimental to the therapeutic efficacy of a device in visual disease applications. Another problem is that some TENS devices deliver rather high initial peak currents, which is a safety concern for applications involving vulnerable or sensitive cells and tissues such as those associated with the retina. In addition, some TENS devices have problems with constant current control, reliability, and electrode interface deficiencies (or contact integrity). Further, most TENS devices are frequency specific, and they deliver most of their power at individual frequencies. For instance, when viewing the signal produced by a device in the frequency domain, the majority of the power output from the signal resides at discrete frequencies. Also, frequency adjustments often must be done manually by the user. Accordingly, the therapeutic effect of the signals generated by these devices is not optimized and is often not consistent.

Another electrotherapeutic device that has been used in visual disease applications is described in U.S. Pat. Nos. 6,035,236 and 6,275,735 to Jarding et al. and entitled "Methods and Apparatus for Electrical Microcurrent Stimulation Therapy." This device includes a waveform generator that generates sweep wave signals that are frequency modulated, i.e., the frequency of the signals varies over time. The waveform generated by this device is simpler in form (i.e., a relatively simple frequency modulated pulse train) compared to the waveforms used in some of the TENS devices and, as such, is compatible with the healing sequence associated with certain visual disease conditions. Also, this device uses a swept frequency approach to waveform modulation that delivers signals over a range of operating frequencies without the need to make any manual frequency adjustments. While this device is better suited for visual disease applications compared to other electrotherapeutic devices, its frequency variations are limited by an analog frequency sweep technique and thus has inherent deficiencies in spectral quality.

BRIEF SUMMARY OF THE INVENTION

The present invention is directed to an electrotherapeutic device that generates at least one waveform for use in microcurrent stimulation therapy to treat patients suffering from macular degeneration and other visual diseases.

In one embodiment, the electrotherapeutic device includes a signal generator configured to generate a hybrid waveform comprising a series of current pulses having a peak current amplitude between 1 microamp and 450 microamps, and typically between 180 microamps and 220 microamps. In this embodiment, three or more waveform parameters of the hybrid waveform are varied in accordance with a protocol for treating a visual disease. The waveform parameters that are varied include, for example, pulse width, pulse period, pulse position, pulse coding, peak current amplitude, duty cycle, and/or pulse shape. In one example, the hybrid waveform comprises a first pulse sequence and a second pulse sequence, wherein the polarity of the first and second pulse sequences is varied to generate a bipolar waveform. The varied waveform parameters of the first pulse sequence may be the same as or different than the varied waveform parameters of the second pulse sequence. The electrotherapeutic device also includes an applicator connected to the signal generator and configured to apply the hybrid waveform to at least one stimulation point within an eye region.

In another embodiment, the electrotherapeutic device includes a signal generator configured to generate a waveform comprising a series of current pulses having a peak current amplitude between 1 microamp and 450 microamps, and typically between 180 microamps and 220 microamps. In this embodiment, the signal generator uses a digital modulation technique that is sequenced to provide the current pulses in accordance with a protocol for treating a visual disease. Preferably, the current pulses are provided at a plurality of discrete frequencies within a defined frequency range of 0.01 Hz to 500 Hz, and typically between 0.1 Hz and 100 Hz. The frequencies are not unnecessarily repeated and more frequencies are provided in the waveform in order to mitigate the spectral content problem discussed above. In one example, the current pulses are provided at 75% or more of the discrete frequencies within a frequency range of 0.3 Hz to 300 Hz. In another example, the current pulses are provided at 75% or more of the discrete frequencies within a frequency range of 0.1 Hz to 50 Hz or a subrange thereof. In yet another example, the current pulses are provided at 75% or more of the discrete frequencies within a frequency range of 0.05 Hz to 10 Hz or a subrange thereof. The therapeutic device also includes an applicator connected to the signal generator and configured to apply the waveform to at least one stimulation point within an eye region.

The therapeutic device of the present invention generates waveforms with spectral characteristics (e.g., various combinations of modulated waveform parameters and/or greater frequency content) that are not provided in the waveforms generated by previous electrotherapeutic devices. The application of these waveforms to at least one stimulation point within an eye region is believed to result in the stabilization or improvement of macular degeneration and other visual diseases.

BRIEF DESCRIPTION OF THE DRAWINGS

Various exemplary embodiments of the present invention are described in detail below with reference to the attached drawing figures, wherein:

FIG. 3B illustrates an exemplary bipolar variable peak current waveform generated by the electrotherapeutic device of FIGS. 1A and 1B, which includes a combination of PAM, PFM and PWM to provide a hybrid waveform;

FIG. 4A illustrates an exemplary waveform generated by a prior art device in which the signal source is controlled using an automatic analog frequency sweep technique;

FIG. 4B illustrates an exemplary hybrid waveform generated by the electrotherapeutic device of FIGS. 1A and 1B in which the signal source is controlled using a digital modulation technique;

DETAILED DESCRIPTION OF EXEMPLARY EMBODIMENTS

The present invention is directed to an electrotherapeutic device that generates at least one waveform for use in microcurrent stimulation therapy to treat patients suffering from macular degeneration and other visual diseases. The device includes a signal source that is directly controlled using a digital modulation technique to generate a waveform that is delivered to tissue of an eye region in accordance with a protocol for treating a visual disease. The spectral characteristics of the waveform (such as various combinations of modulated waveform parameters and/or greater frequency content, as discussed below) are believed to result in the stabilization or improvement of macular degeneration and other visual diseases.

While the invention will be described in detail below with reference to various exemplary embodiments, it should be understood that the invention is not limited to the specific device configuration, waveforms, waveform parameters (pulse width, pulse period, pulse position, pulse coding, peak current amplitude, duty cycle, and/or pulse shape), or methodologies of these embodiments. In addition, although the exemplary embodiments are described as embodying several different inventive features, one skilled in the art will appreciate that any one of these features could be implemented without the others in accordance with the present invention.

Electrotherapeutic Device

Figure 1A:
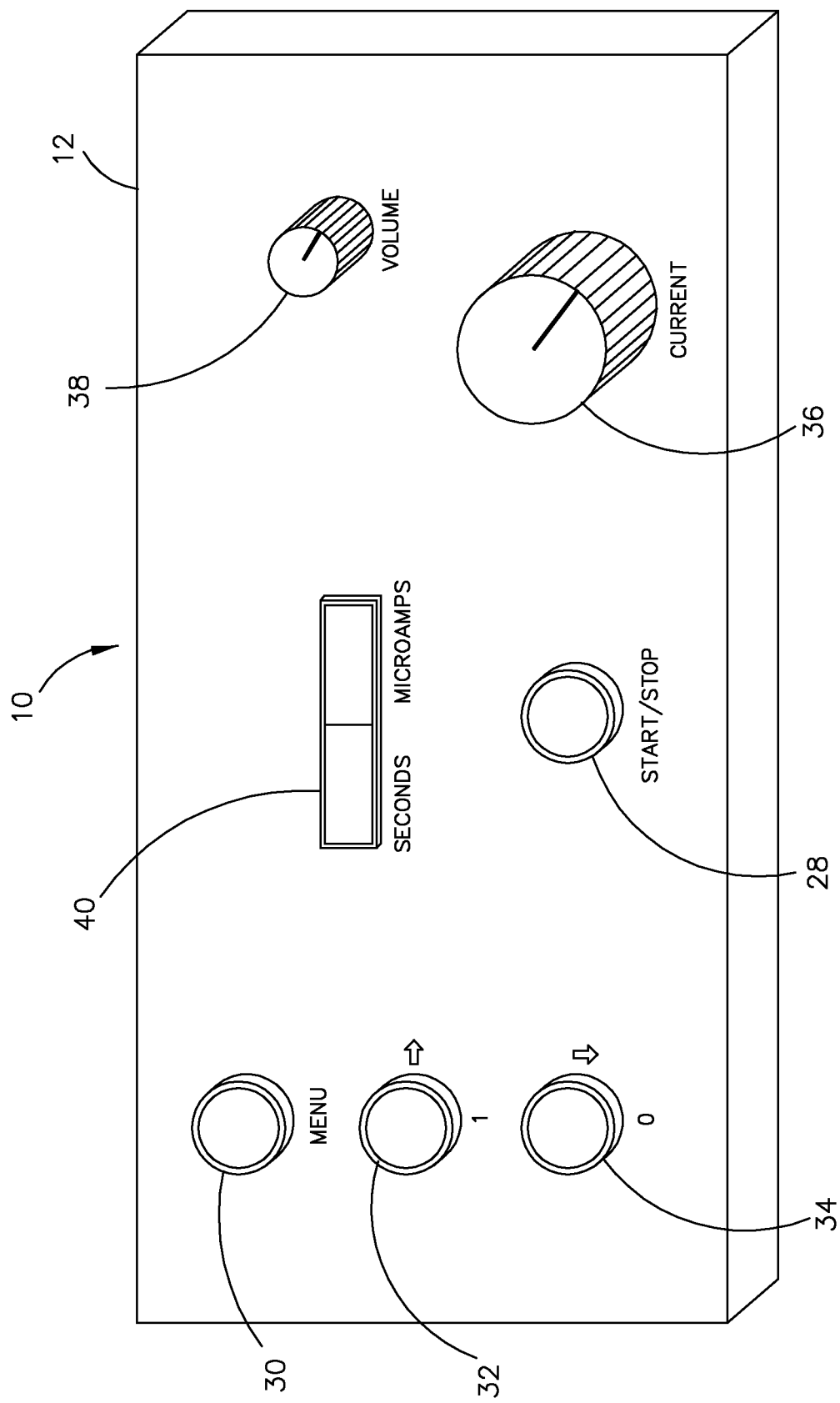
FIG. 1A illustrates the front panel of an electrotherapeutic device in accordance with an exemplary embodiment of the present invention.
Figure 1B:
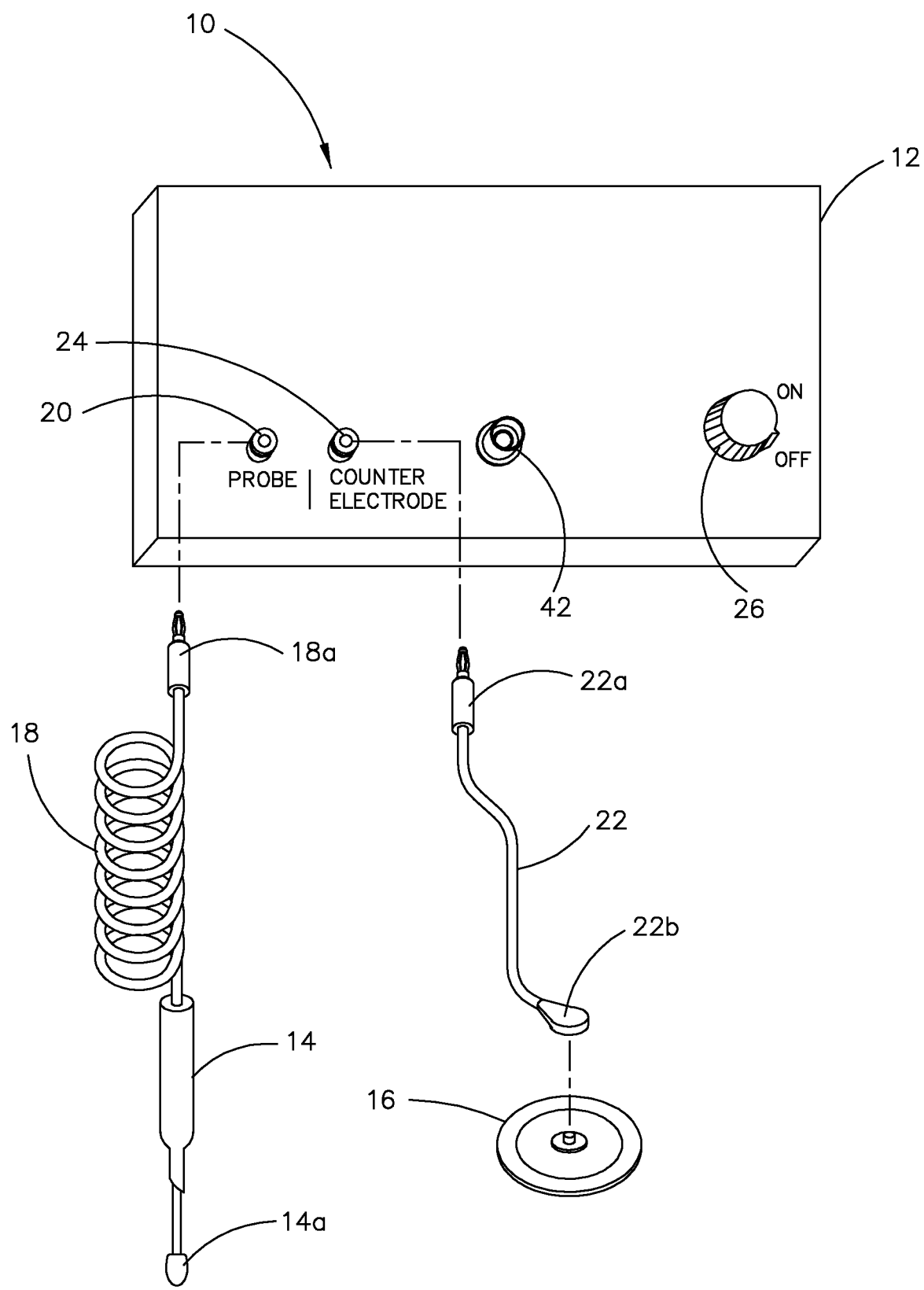
FIG. 1B illustrates the back panel of the electrotherapeutic device of FIG. 1.

With reference to FIGS. 1A and 1B, an electrotherapeutic device in accordance with an exemplary embodiment of the present invention is shown as reference numeral 10. Electrotherapeutic device 10 comprises a signal generator 12 that generates at least one waveform (described in greater detail below) and, as shown in FIG. 1B, an applicator comprising a stimulation probe 14 and a counter electrode 16. Stimulation probe 14 is attached to an electrical connector 18 that is connectable to a probe connection 20 located on the back panel of signal generator 12. Similarly, counter electrode 16 is attached to an electrical connector 22 that is connectable to a counter electrode connection 24 located on the back panel of signal generator 12. Also provided on the back panel of signal generator 12 is an on/off switch 26 that enables an operator to power on and power off the device. The device preferably operates on batteries, but may also be connected to an electrical wall outlet for its source of power.

Referring still to FIG. 1B, stimulation probe 14 comprises a shielded hand-held probe configured to administer microcurrent stimulation to tissue of an eye region, and typically to tissue on or near a closed eyelid of a patient. Probe 14 includes a probe tip 14a that, in its most basic configuration, comprises a cotton swab moistened or dampened with a conductive gel, hydrogel and/or semiconducting polymer material. The dampened cotton swab allows for the gentle administration of microcurrent to the patient without undue discomfort. Of course, one skilled in the art will appreciate that other types of probe tips may also be used in accordance with the present invention. For example, probe tip 14a may be made from a variety of different metals such as medical grade stainless steel, gold-plated brass, other metal combinations or other conductive materials. Also, one skilled in the art will appreciate that the probe structure is not limited to a single electrode contact.

In the exemplary embodiment, electrical connector 18 comprises a stretchable coiled wire with one end connected to stimulation probe 14 and the other end having a banana plug 18a. Probe connection 20 comprises a banana jack for receiving the banana plug 18a. As such, probe 14 may be easily connected to signal generator 12 via the stretchable coiled wire and banana connection. Of course, one skilled in the art will appreciate that other types of electrical connectors may be used to connect probe 14 to signal generator 12 in accordance with the present invention. For example, it is possible to use a lead wire of sufficient length instead of a coiled wire and/or a pin connector instead of a banana connector. Alternatively, probe 14 may be hardwired to signal generator 12.

Counter electrode 16 comprises an electrode that is configured for attachment to a body part of a patient. In the exemplary embodiment, counter electrode 16 comprises a snap electrode that may be secured with adhesive to the patient's right temple. Of course, one skilled in the art will appreciate that other types of electrodes and/or more than one electrode may be used in accordance with the present invention. Also, counter electrode 16 may be secured to other parts of the body, such as the back of the neck or head, the shoulder, the arm, the wrist, or the hand.

In the exemplary embodiment, electrical connector 22 comprises a lead wire with one end having a snap connector 22b that may be attached to the counter electrode 16 (which is a snap electrode in this embodiment) and the other end having a banana plug 22a. Counter electrode connection 24 comprises a banana jack for receiving the banana plug 22a. As such, counter electrode 16 may be easily connected to signal generator 12 via the lead wire and banana connection. Of course, one skilled in the art will appreciate that other types of electrical connectors may also be used to connect counter electrode 16 to signal generator 12 in accordance with the present invention. For example, it is possible to use a pin connector instead of a banana connector. Alternatively, counter electrode 16 may be hardwired to signal generator 12.

As shown in FIG. 1A, the front panel of signal generator 12 includes a variety of buttons, knobs, dials and the like to facilitate easy use and control of the device. For example, a start/stop button 28 is provided that enables an operator to begin or end a treatment session. There is also a menu system that includes a main menu button 30, a left/right navigation button 32 that enables an operator to move left and right within the menu system, and an up/down navigation button 34 that enables an operator to move up and down within the menu system. While the menu system may enable an operator to adjust certain treatment parameters, it is preferred to minimize the number of available adjustments for consistency in therapeutic efficacy. For example, in the exemplary embodiment, frequency range adjustments and course adjustments in the peak current of the waveform generated by signal generator 12 may be made in the menu system, along with the number of individual treatments and treatment duration for the treatment session. The menu system may also enable an operator to select one of a plurality of pre-programmed treatment protocols that have been loaded on the device via software or firmware. However, the device preferably only provides a single treatment protocol that is designed specifically for a particular visual disease.

A current control dial 36 is also provided that enables an operator to make fine adjustments in the peak current of the waveform generated by signal generator 12. There is also a volume dial 38 that enables a user to adjust the volume of the auditory output generated by a built-in speaker within the device. Examples of the types of auditory outputs that may be produced by the device include a start beep to indicate the beginning of a treatment session, a stop beep to indicate the end of a treatment session, and a current tracking beep sequence (e.g., periodic beeps) to indicate that current is being provided during a treatment session.

A display 40 is further provided that displays one or more treatment session parameters. In the exemplary embodiment, display 40 comprises a two-parameter display with a treatment duration indicator and a current level indicator. The treatment duration indicator provides information on the duration of the treatment session, and preferably resets each time that stimulation probe 14 is applied to a stimulation point on a patient and counts down in seconds for each point of application (discussed further below with reference to FIG. 7). The current level indicator enables an operator to monitor the average or peak current being supplied to the patient. Of course, one skilled in the art will appreciate that other types of treatment information may also be displayed in accordance with the present invention.

Referring again to the back panel of signal generator 12 in FIG. 1B, a testing connection 42 is provided for connection to one or more oscilloscopes, spectrum analyzers or waveform displays. This connection enables the current level and other waveform parameters to be monitored at various locations within the generator circuit for testing purposes. Further, while not illustrated in the figures, signal generator 12 may provide output ports for connection to an external data analysis system and/or a billing system. In accordance with this aspect of the invention, signal generator 12 preferably is configured to record various types of data or information on instrument use for different patients, and then download the data to the data analysis system and/or the billing system. In this manner, a doctor or practitioner can analyze data concerning variations in current levels and other waveform parameters for a particular patient or between patients and for different visual diseases and disease states. The doctor or practitioner can then use this data to track therapy progress for a particular patient, develop better therapy procedures for different visual diseases, and monitor variabilities in treatment points. In addition, the device provides cost analysis and throughput optimization capabilities, and enables the transmission of information for billing purposes.

Of course, while signal generator 12 has been described above as providing different control features and device outputs, one skilled in the art will appreciate that certain control features or device outputs may be eliminated and other control features and device outputs may be added in accordance with the present invention.

Referring now to FIGS. 2A-2E, 3A-3B and 4A-4D, a detailed description of signal generator 12 will now be provided (and a description of the circuit will be described below with reference to FIG. 5). In general terms, signal generator 12 is configured to automatically generate at least one waveform comprising a series of current pulses at variable current amplitudes and treatment durations. The waveform generated by signal generator 12 includes a variety of waveform parameters associated with the series of current pulses, including pulse width, pulse period (which determines the frequency), pulse position within a pulse period, pulse coding (if any), peak current amplitude, duty cycle, pulse shape, and polarity (e.g., unipolar or bipolar). As discussed below, any one of these waveform parameters or any combination of these waveform parameters may be modulated or varied in accordance with a protocol for treating a visual disease to generate a waveform in accordance with the present invention.

Examples of the types of pulse modulation techniques that may be used to modulate or vary the waveform parameters are shown generally in FIGS. 2A-2E, wherein the modulating signal wave is shown as a dashed sine wave in each of the figures. For each example, the peak current amplitude (I) is shown in the ordinate direction and time (t) is shown along the abscissa. Of course, one skilled in the art will appreciate that the pulse modulation techniques described below are merely examples and that other types of pulse modulation techniques may also be used in accordance with the present invention.

Figure 2A:
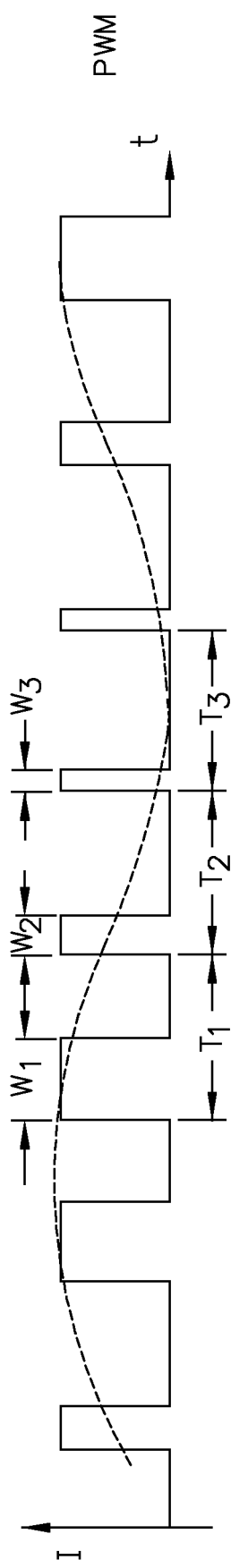
FIG. 2A illustrates a series of current pulses that have been modulated using a pulse width modulation (PWM) technique.

FIG. 2A shows an example of a pulse width modulation (PWM) technique in which the pulse width (W) is modulated or varied between different pulse periods (T). For example, it can be seen that pulse width $W_1$ within pulse period $T_1$ is greater than pulse width $W_2$ within pulse period $T_2$ and, similarly, pulse width $W_2$ within pulse period $T_2$ is greater than pulse width $W_3$ within pulse period $T_3$. Note that the peak current amplitude of the pulses, the position of the pulses, and the pulse period (which determines the frequency) remain constant in this example.

Figure 2B:
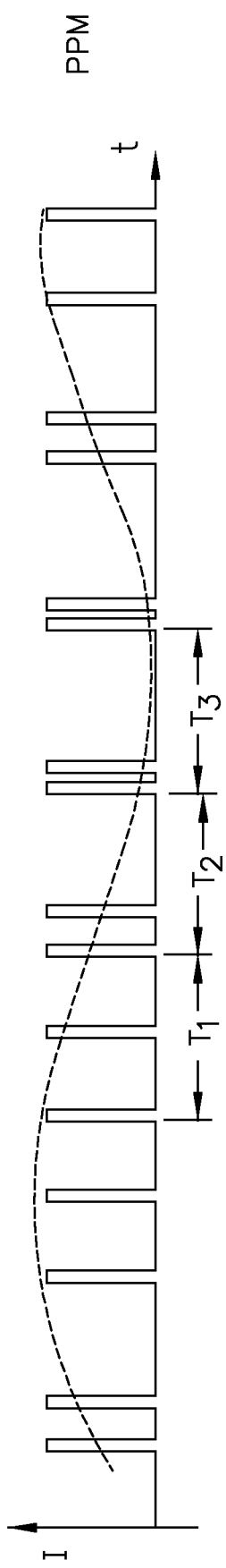
FIG. 2B illustrates a series of current pulses that have been modulated using a pulse position modulation (PPM) technique.

FIG. 2B shows an example of a pulse position modulation (PPM) technique in which the position of the individual pulses is modulated or varied between different pulse periods (T). For example, it can be seen that pulse periods $T_1$, $T_2$ and $T_3$ each include two pulses, the first of which is positioned at the beginning of the pulse period. However the position of the second pulse is varied between the different pulse periods, i.e., the time delay between the first and second pulses in pulse period $T_1$ is greater than the time delay between the first and second pulses in pulse period $T_2$ and, similarly, the time delay between the first and second pulses in pulse period $T_2$ is greater than the time delay between the first and second pulses in pulse period $T_3$. Note that the peak current amplitude of the pulses, the width of the pulses, and the pulse period (which determines the frequency) remain constant in this example.

Figure 2C:
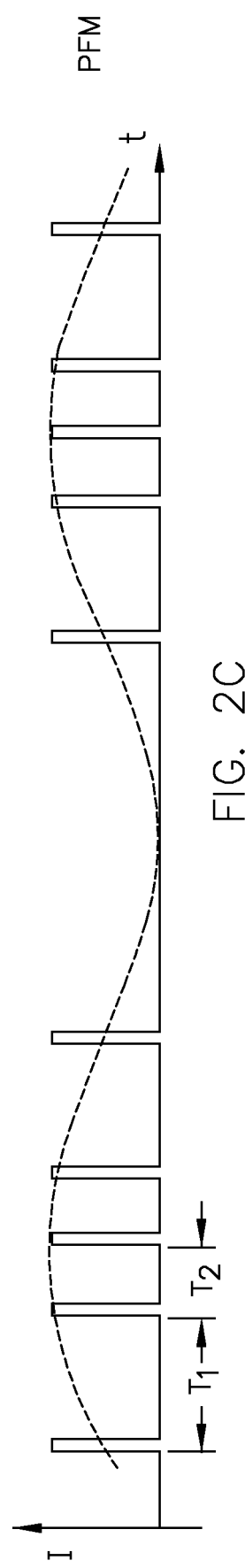
FIG. 2C illustrates a series of current pulses that have been modulated using a pulse frequency modulation (PFM) technique.

FIG. 2C shows an example of a pulse frequency modulation (PFM) technique in which the pulse period (T) (which determines the frequency) is modulated or varied. For example, it can be seen that the pulse period $T_1$ is greater than the pulse period $T_2$. Note that the peak current amplitude of the pulses, the width of the pulses, and the position of the five pulses within each positive half cycle of the sine wave remain constant in this example.

Figure 2D:
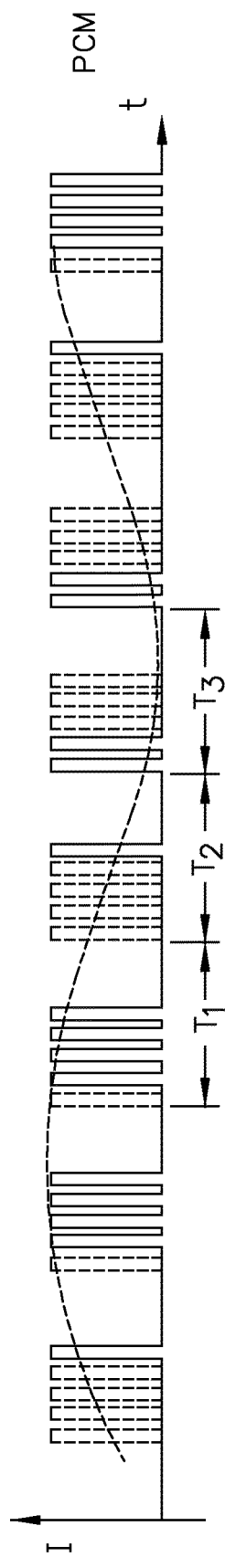
FIG. 2D illustrates a series of current pulses that have been modulated using a pulse code modulation (PCM) technique.

FIG. 2D shows an example of a pulse code modulation (PCM) technique in which the pulses are provided in a code format. For example, it can be seen that there are five possible pulses within each pulse period (T) that can either be either "on" or "off." In this example, pulses 2-5 are "on" in pulse period $T_1$, pulse 5 is "on" in pulse period $T_2$, and pulses 1 and 2 are "on" in pulse period $T_3$. Note that the peak current amplitude of the pulses, the width of the pulses, the position of the five possible pulses, and the pulse period (which determines the frequency) remain constant in this example.

Figure 2E:
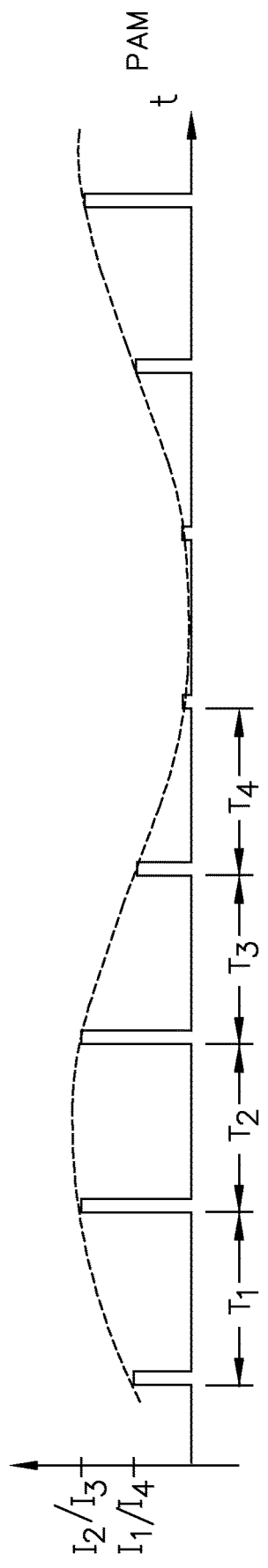
FIG. 2E illustrates a series of current pulses that have been modulated using a pulse amplitude modulation (PAM) technique.

FIG. 2E shows an example of a pulse amplitude modulation (PAM) technique in which the peak current amplitude (I) of the pulses is modulated or varied between different pulse periods (T). For example, it can be seen that peak current amplitude $I_1$ within pulse period $T_1$ is less than peak current amplitude $I_2$ within pulse period $T_2$, and, peak current amplitude $I_3$ within pulse period $T_3$ is greater than peak current amplitude $I_4$ within pulse period $T_4$. (in this example, $I_1=I_4$ and $I_2=I_3$). Note that the width of the pulses, the position of the pulses, and the pulse period (which determines the frequency) remain constant in this example.

Further, it should be noted that certain combinations of pulse modulation techniques may provide a phase delay. For example, with reference to FIGS. 2B and 2C, a phase delay can be seen by comparing the pulses in the PPM pulse train with the pulses in the PFM pulse train. Note that the second to last PPM pulse occurs after the second to last PFM pulse, but the last PPM pulse occurs at the same time as the last PFM pulse. With periodic signals, time in seconds is converted to phase in radians and, as such, a time delay corresponds to a phase delay. This phase delay (which could be considered a different version of pulse position modulation) may be used in certain waveforms in accordance with the present invention.

It should be understood that the pulse modulation techniques described and illustrated above with reference to FIGS. 2A-2E are provided only to show the different types of waveform parameters that can be modulated or varied in accordance with the present invention. The actual waveforms shown in FIGS. 2A-2E are not desired due to the low duty cycle of the waveforms, which results in low average currents and low energies. It is known that therapeutic efficacy drops off with average currents below 70 microamps. As such, the peak currents for the waveforms shown in FIGS. 2A-2E would have to be quite high to maintain an acceptable average current level, which is not desired for visual disease applications due to safety concerns.

As discussed above, the waveform generated by signal generator 12 comprises a series of current pulses having a variety of different waveform parameters, including pulse width, pulse period (which determines the frequency), pulse position within a pulse period, pulse coding (if any), peak current amplitude, duty cycle, pulse shape, and polarity (e.g., unipolar or bipolar). In the exemplary embodiment, the width of the pulses is in the range of 1.43 milliseconds to 10 seconds, and typically between 10 milliseconds and 1 second. Also, the full pulse period is in the range of 2 milliseconds to 100 seconds, corresponding to a frequency in the range of 0.01 Hz to 500 Hz. Typically, the output frequency is between 0.1 Hz and 100 Hz for visual disease applications. In addition, the peak current amplitude of the pulses is in the range of 1 microamp to 450 microamps, and typically between 180 microamps and 220 microamps.

The waveform has a duty cycle in the range of 10% to 90%, and typically between 50% and 75%. Also, the waveform has an average current in the range of 70 microamps to 200 microamps, and typically between 90 microamps and 100 microamps for visual disease applications. One skilled in the art will appreciate that the average current is dependent on the peak current amplitude and the duty cycle of the waveform. For example, in a constant peak current waveform, the average current increases as the duty cycle increases. The shape of each of the current pulses is generally rectangular, wherein the edges of the rectangular pulses are preferably trapezoidal and/or exponentially rounded (no sharp corners) to minimize spiking. Each waveform may be unipolar (single polarity) or bipolar (dual polarity). Of course, one skilled in the art will appreciate that other values, ranges and pulse shapes for the above-described waveform parameters may be used in accordance with the present invention.

In accordance with the invention, any one of the above-described waveform parameters or any combination of these waveform parameters may be modulated or varied in accordance with a protocol for treating a visual disease. It should be understood that the number of different waveforms that can be generated is quite large. For example, it can be appreciated that three waveform parameters—pulse width, pulse period (which determines the frequency), and pulse position—may be varied in different combinations to generate seven different exemplary waveforms: (1) a waveform in which only the pulse width is varied; (2) a waveform in which only the pulse period is varied; (3) a waveform in which only the pulse position is varied; (4) a waveform in which the pulse width and pulse period are varied; (5) a waveform in which the pulse width and pulse position are varied; (6) a waveform in which the pulse period and pulse position are varied, and (7) a waveform in which the pulse width, pulse period, and pulse position are varied. Of course, one skilled in the art will appreciate that other waveform parameters and combinations of waveform parameters may be modulated or varied to generate other exemplary waveforms in accordance with the present invention.

Further, the waveform generated by signal generator 12 may have a plurality of pulse sequences that may or may not be separated by periods of non-current flow. Each pulse sequence comprises a plurality of current pulses with waveform parameters that may be the same as or different from the waveform parameters of other pulse sequences in the waveform. For example, the waveform shown in FIG. 3A (discussed below) is comprised of two pulse sequences with the same waveform parameters other than polarity (i.e., the polarity of the current pulses is reversed with each successive sequence). Further, the pulse sequences can be varied to include linear, nonlinear, random or chaotic features in the modulation format.

Figure 3A:
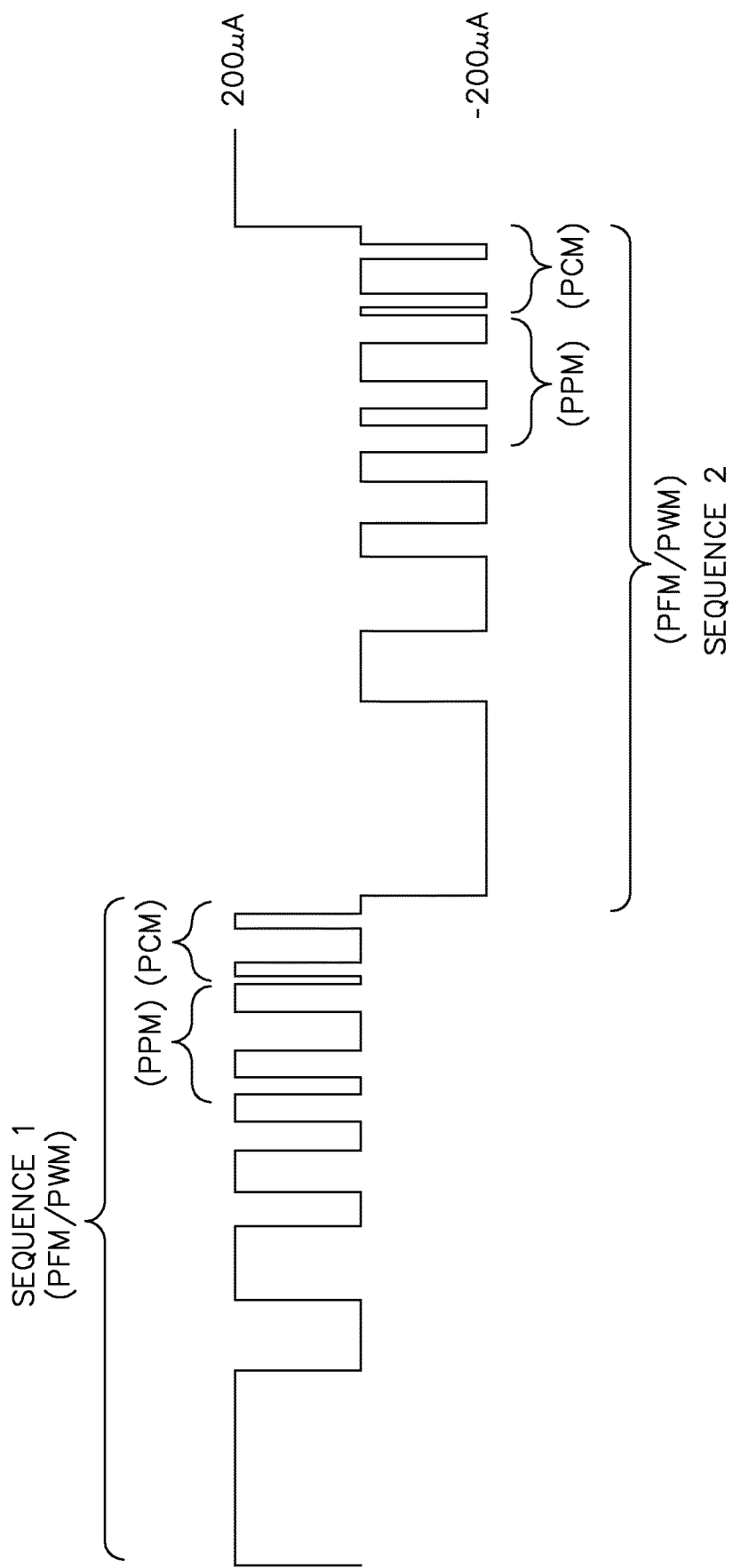
FIG. 3A illustrates an exemplary bipolar constant peak current waveform generated by the electrotherapeutic device of FIGS. 1A and 1B, which includes a combination of PFM, PWM, PPM and PCM to provide a hybrid waveform.

Without limiting the generality of the foregoing description, FIG. 3A shows an exemplary hybrid waveform consisting of a bipolar constant peak current waveform in which the waveform parameters of the positive and negative polarity pulse sequences are identical. The positive polarity pulse sequence is identified as "Sequence 1" and the negative polarity pulse sequence is identified as "Sequence 2." Each of the pulse sequences is provided in a time period of about 10 to 20 seconds. In this example, each pulse sequence is generated using a digital modulation technique that provides combinations of pulse frequency modulation (PFM), pulse width modulation (PWM), pulse position modulation (PPM), and pulse code modulation (PCM), as shown.

FIG. 3B shows another exemplary hybrid waveform consisting of a bipolar variable peak current waveform in which the waveform parameters of the positive and negative polarity pulse sequences are identical. The positive polarity pulse sequence is identified as "Sequence 1" and the negative polarity pulse sequence is identified as "Sequence 2." Again, each of the pulse sequences is provided in a time period of about 10 to 20 seconds. In this example, each pulse sequence is generated using a digital modulation technique that provides combinations of pulse amplitude modulation (PAM), pulse frequency modulation (PFM), and pulse width modulation (PWM), as shown.

One skilled in the art will appreciate that the hybrid waveforms shown in FIGS. 3A and 3B are just examples and that other hybrid waveforms may also be generated in accordance with the present invention. Also, the positive and negative polarity pulse sequences of the waveforms are not necessarily confined to being identical (which is the case with the waveforms shown in FIGS. 3A and 3B) and could be different with respect to pulse modulation combinations, frequency range, sequence length, etc.

It should be understood that the various types of waveforms that may be generated by signal generator 12 in accordance with the present invention provide spectral characteristics that are not provided in the waveforms generated by previous electrotherapeutic devices. These spectral characteristics (such as various combinations of modulated waveform parameters and/or greater frequency content, as discussed below) are believed to result in the stabilization or improvement of macular degeneration and other visual diseases. In order to illustrate this aspect of the invention, reference is made to the comparison of waveforms shown in FIGS. 4A and 4B.

FIG. 4A is a bipolar constant peak current waveform generated by the TheraMac device developed by Acuity Medical International, Inc. This device utilizes an analog frequency sweep technique in which an analog voltage frequency modulates the oscillations of a voltage controlled oscillator (VCO) to generate a waveform that is frequency modulated within a defined frequency range. However, in the waveform generating using this analog frequency sweep technique, frequencies are often repeated and large ranges of frequencies (spectral content) are completely missing.

FIG. 4B is an exemplary bipolar constant peak current waveform generated by signal generator 12 in accordance with the present invention. Signal generator 12 includes a signal source that is directly controlled using a digital modulation technique (discussed below) that causes modulation of one or more waveform parameters (in this example, the modulated waveform parameters are pulse width, pulse position, and pulse frequency) in such a manner that there are more pulse modulation signal components visible than those of the waveform shown in FIG. 4A. Unlike the waveform shown in FIG. 4A, frequencies are not unnecessarily repeated and more frequencies are provided in the waveform in order to mitigate the spectral content problem discussed above. In other words, signal generator 12 is not as susceptible to the frequency range limitations and the level of spectral defects that can occur with the analog frequency sweep technique.

As just discussed, the frequency variations provided by the TheraMac device are limited by an analog frequency sweep technique and, thus, the waveform has inherent deficiencies in spectral quality. By contrast, signal generator 12 uses a digital modulation technique that is sequenced to provide 75% or more (e.g., 75%, 76%, 77%, 78%, 79%, 80%, 81%, 82%, 83%, 84%, 85%, 86%, 87%, 88%, 89%, 90% or more) of the discrete frequencies within a defined frequency range. It should be understood that the defined frequency range will vary between different treatments and, generally, will fall within the frequency range of 0.01 Hz to 500 Hz, and typically between 0.1 Hz and 100 Hz for visual disease applications.

In the exemplary embodiment, signal generator 12 provides a wide-band operating mode, a mid-band operating mode, and a narrow-band operating mode that are programmed into the device to provide different ranges of frequency coverage for patients who respond to slightly different frequencies.

In the wide-band operating mode, the generator provides a waveform consisting of four 10 to 20 second pulse sequences (i.e., a 40 to 80 second treatment) in which the individual pulses within each sequence change in frequency with time between a lower limit of about 0.3 pulses per second to an upper limit of about 300 pulses per second, i.e., a frequency range between 0.3 Hz and 300 Hz. Preferably, the current pulses are provided at 75% or more (e.g., 75%, 76%, 77%, 78%, 79%, 80%, 81%, 82%, 83%, 84%, 85%, 86%, 87%, 88%, 89%, 90% or more) of the discrete frequencies within the frequency range of 0.3 Hz to 300 Hz.

In the mid-band operating mode, the generator provides a waveform consisting of four 10 to 20 second pulse sequences (i.e., a 40 to 80 second treatment) in which the individual pulses within each sequence change in frequency with time between a lower limit of about 0.1 pulses per second to an upper limit in the range of about 10 to 50 pulses per second, i.e., a frequency range between 0.1 Hz and 10 to 50 Hz. Preferably, the current pulses are provided at 75% or more (e.g., 75%, 76%, 77%, 78%, 79%, 80%, 81%, 82%, 83%, 84%, 85%, 86%, 87%, 88%, 89%, 90% or more) of the discrete frequencies within the frequency range of 0.1 Hz to 50 Hz or a subrange thereof (e.g., 0.1 Hz to 50 Hz, 0.1 Hz to 45 Hz, 0.1 Hz to 40 Hz, 0.1 Hz to 35 Hz, 0.1 Hz to 30 Hz, 0.1 Hz to 25 Hz, 0.1 Hz to 20 Hz, 0.1 Hz to 15 Hz, 0.1 Hz to 10 Hz, etc.).

In the narrow-band operating mode, the generator provides a waveform consisting of four 10 to 20 second pulse sequences (i.e., a 40 to 80 second treatment) in which the individual pulses within each sequence change in frequency with time between a lower limit of about 0.05 pulses per second to an upper limit in the range of about 1 to 10 pulses per second, i.e., a frequency range between 0.05 Hz and 1 to 10 Hz. Preferably, the current pulses are provided at 75% or more (e.g., 75%, 76%, 77%, 78%, 79%, 80%, 81%, 82%, 83%, 84%, 85%, 86%, 87%, 88%, 89%, 90% or more) of the discrete frequencies within the frequency range of 0.05 Hz to 10 Hz or a subrange thereof (e.g., 0.05 Hz to 10 Hz, 0.05 Hz to 9 Hz, 0.05 Hz to 8 Hz, 0.05 Hz to 7 Hz, 0.05 Hz to 6 Hz, 0.05 Hz to 5 Hz, 0.05 Hz to 4 Hz, 0.05 Hz to 3 Hz, 0.05 Hz to 2 Hz, 0.05 Hz to 1 Hz, etc.).

In addition, signal generator 12 preferably provides a "hold" operating mode in order to provide certain frequencies or pulse rates that are believed to have an enhanced effect on specific biochemical events, processes or mechanisms-of-action. For example, direct current is believed to have a significant impact on adenosine triphosphate (ATP) production/release, frequencies at or below 1 Hz are believed to have an effect on electro-osmosis and influence fluid transport (to help relieve the stress of macular edema in diabetic retinopathy), and 10 Hz is believed to have an effect on DNA replication. This "hold" operating mode may be utilized to momentarily focus the therapeutic effort on a particular problem associated with a particular visual disease or unique to a particular visual disease.

Referring now to FIGS. 8A-8I, another exemplary hybrid waveform generated by signal generator 12 that is believed to be therapeutically efficacious for treating macular degeneration will be described. This waveform comprises a 40-second bipolar constant peak current waveform comprising a first 10-second pulse sequence having a positive polarity, a second 10-second pulse sequence having a negative polarity, a third 10-second pulse sequence having a positive polarity, and a fourth 10-second pulse sequence having a negative polarity. The waveform parameters of the positive and negative polarity pulse sequences are identical.

Figure 6:
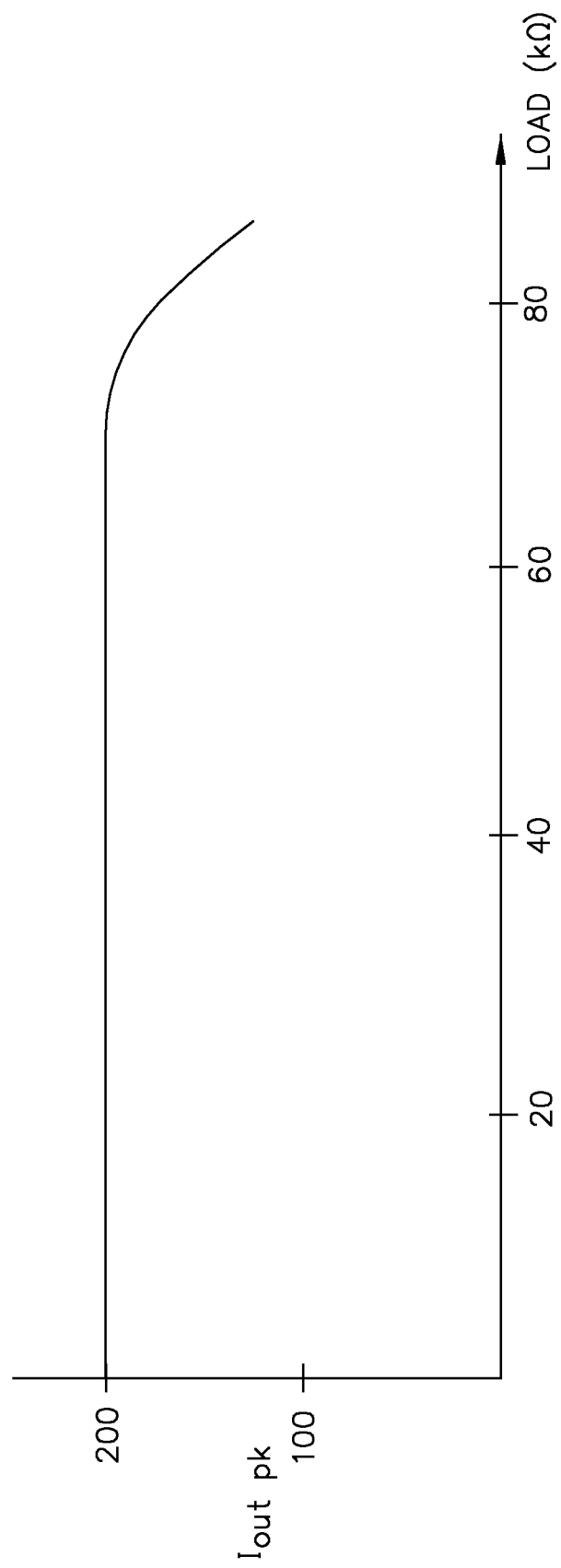
FIG. 6 illustrates the output current levels for the signal generator circuit of FIG. 5 in relation to a range of load impedances.
Figure 7:
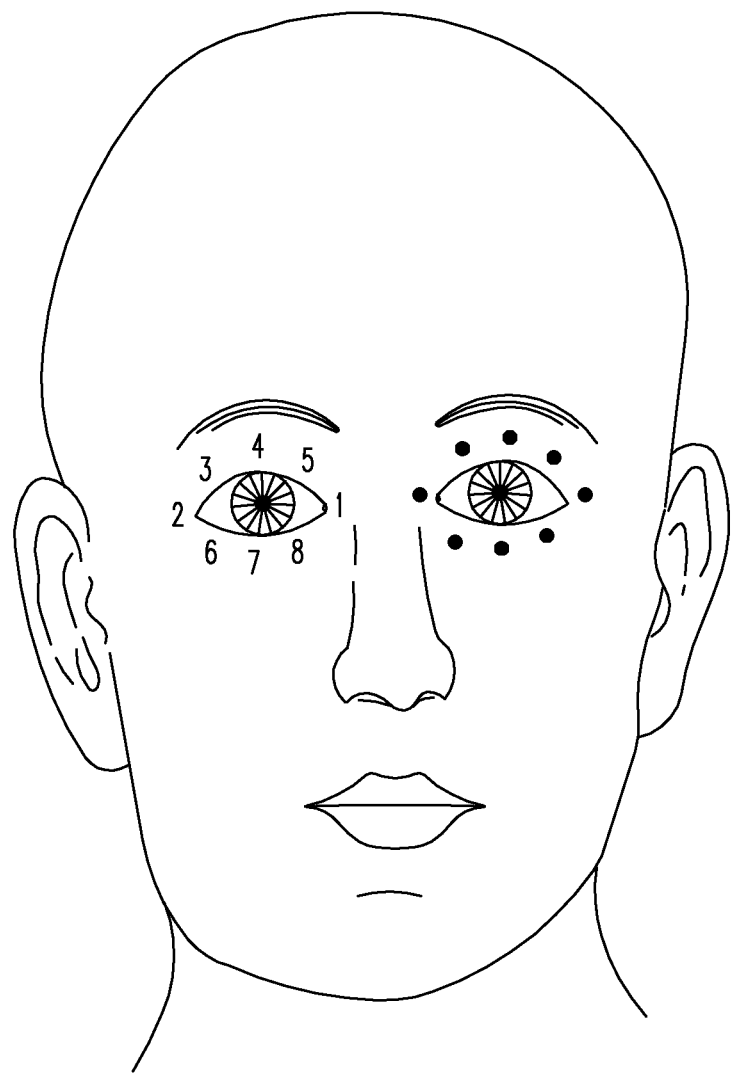
FIG. 7 illustrates eight stimulation points on and around a closed eyelid to which a waveform generated by the electrotherapeutic device of FIGS. 1A and 1B may be applied in accordance with an exemplary method for treating visual disease.
Figure 8A:
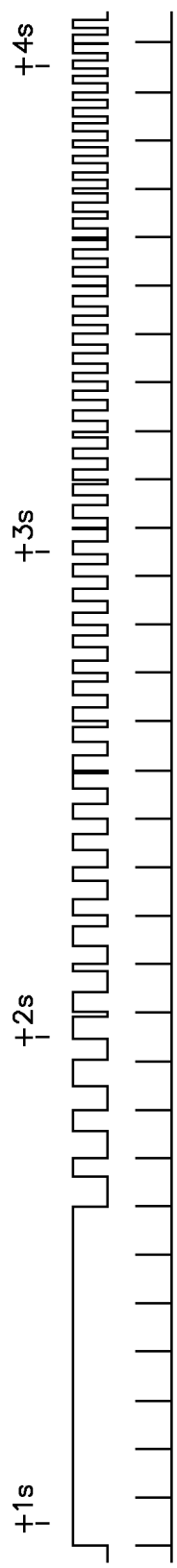
FIGS. 8A-8I illustrate a 10-second pulse sequence of an exemplary hybrid waveform generated by the electrotherapeutic device of FIGS. 1A and 1B.
Figure 8B:
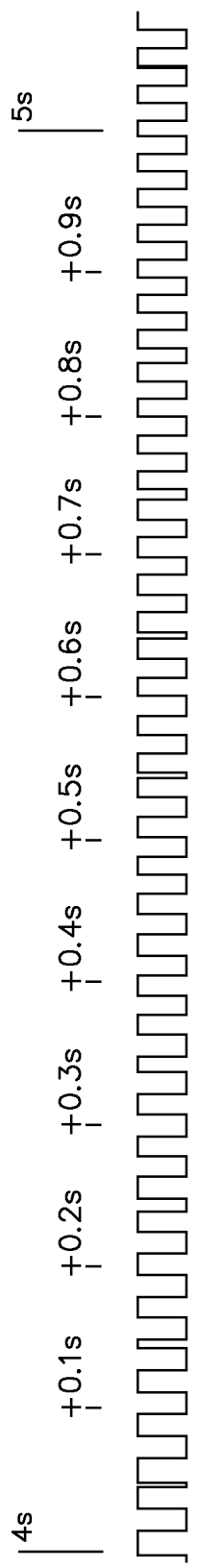
Figure 8C:
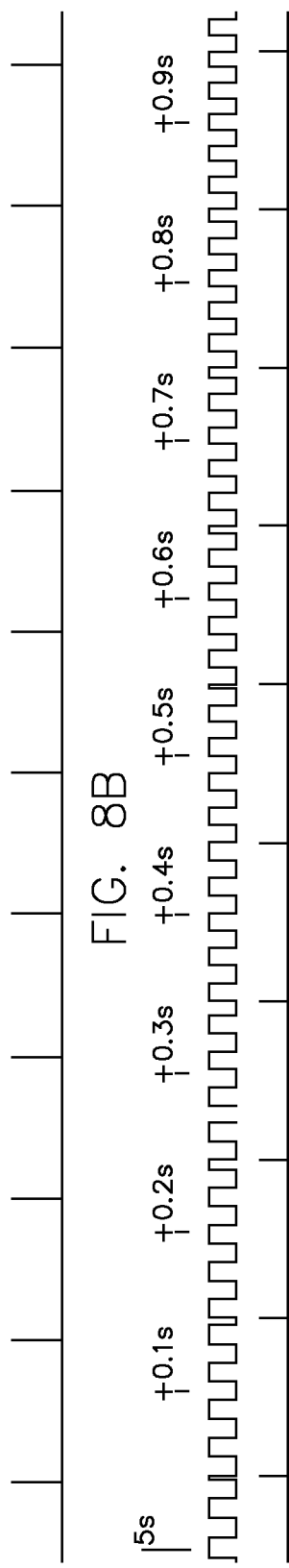
Figure 8D:
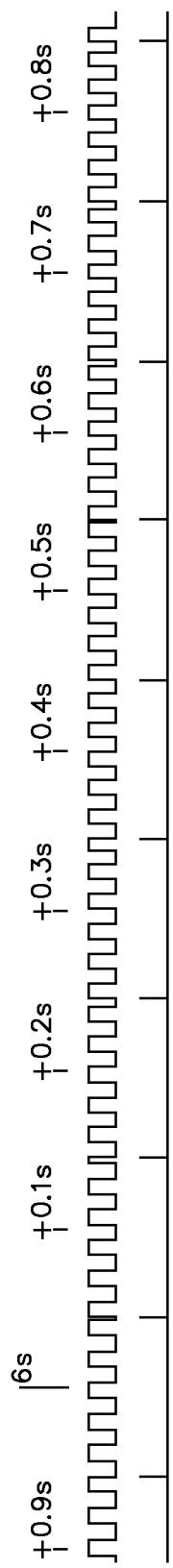
Figure 8E:
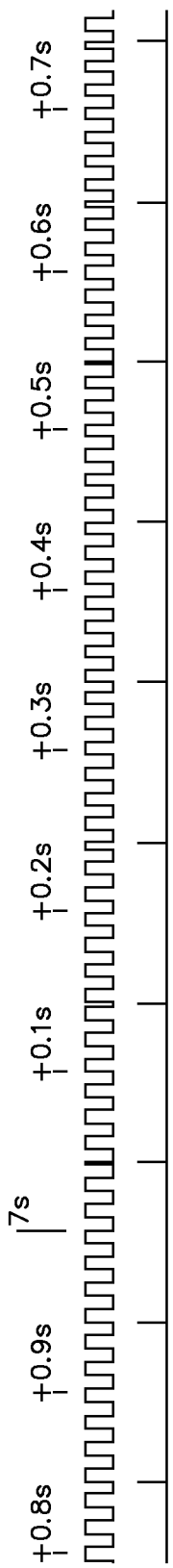
Figure 8F:
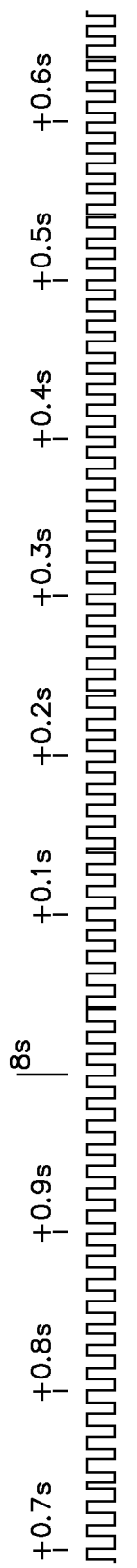
Figure 8G:
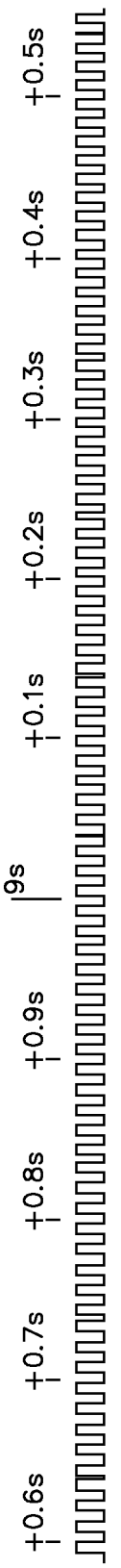
Figure 8H:
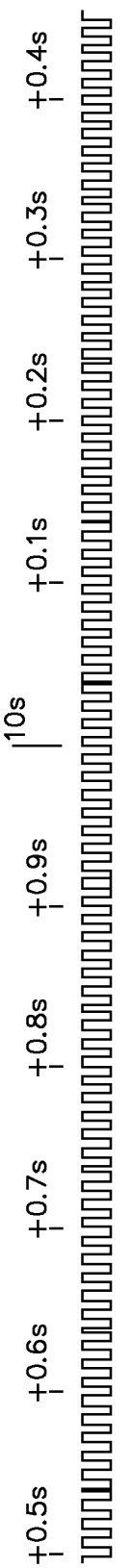
Figure 8I:
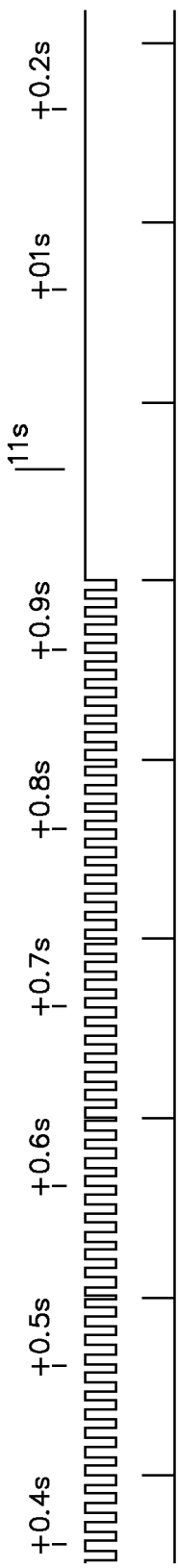

The first 10-second pulse sequence is shown in FIGS. 8A-8I, i.e., the current pulses between the timing marks shown as 1 second (1 s) and 11 seconds (11 s) in the figures. Specifically, 1 second to 4 seconds is shown in FIG. 8A, 4 seconds to 5 seconds is shown in FIG. 8B (4 s to 5 s), 5 seconds to 5.9 seconds is shown in FIG. 8C, 5.9 seconds to 6.8 seconds is shown in FIG. 8D, 6.8 seconds to 7.7 seconds is shown in FIG. 8E, 7.7 seconds to 8.6 seconds is shown in FIG. 8F, 8.6 seconds to 9.5 seconds is shown in FIG. 8G, 9.5 seconds to 10.4 seconds is shown in FIG. 8H, and 10.4 seconds to 11 seconds is shown in FIG. 8I. Of course, it should be understood that each of the second, third and fourth pulse sequences is identical to that shown in FIGS. 8A-8I (with the exception that the second and fourth pulse sequences have a negative polarity).

The current pulses shown in FIGS. 8A-8I are generated by signal generator 12 using a digital modulation technique that provides combinations of pulse frequency modulation (PFM), pulse width modulation (PWM), pulse position modulation (PPM), and pulse code modulation (PCM), as shown. It should be noted that the beginning of the waveform provides a very short burst of current (about 0.699 seconds) for a little extra emphasis on DC, which has been shown to be beneficial in treating visual disease. Thereafter, the current pulses are provided at different frequencies that can be approximated by the equation $f=[10+(9.68)(t')]$, where f is the frequency in Hz and t' is the time in seconds starting from the end of the 0.699 second pulse (i.e., $t'=0$ at the end of the 0.699 second pulse).

Figure 5:
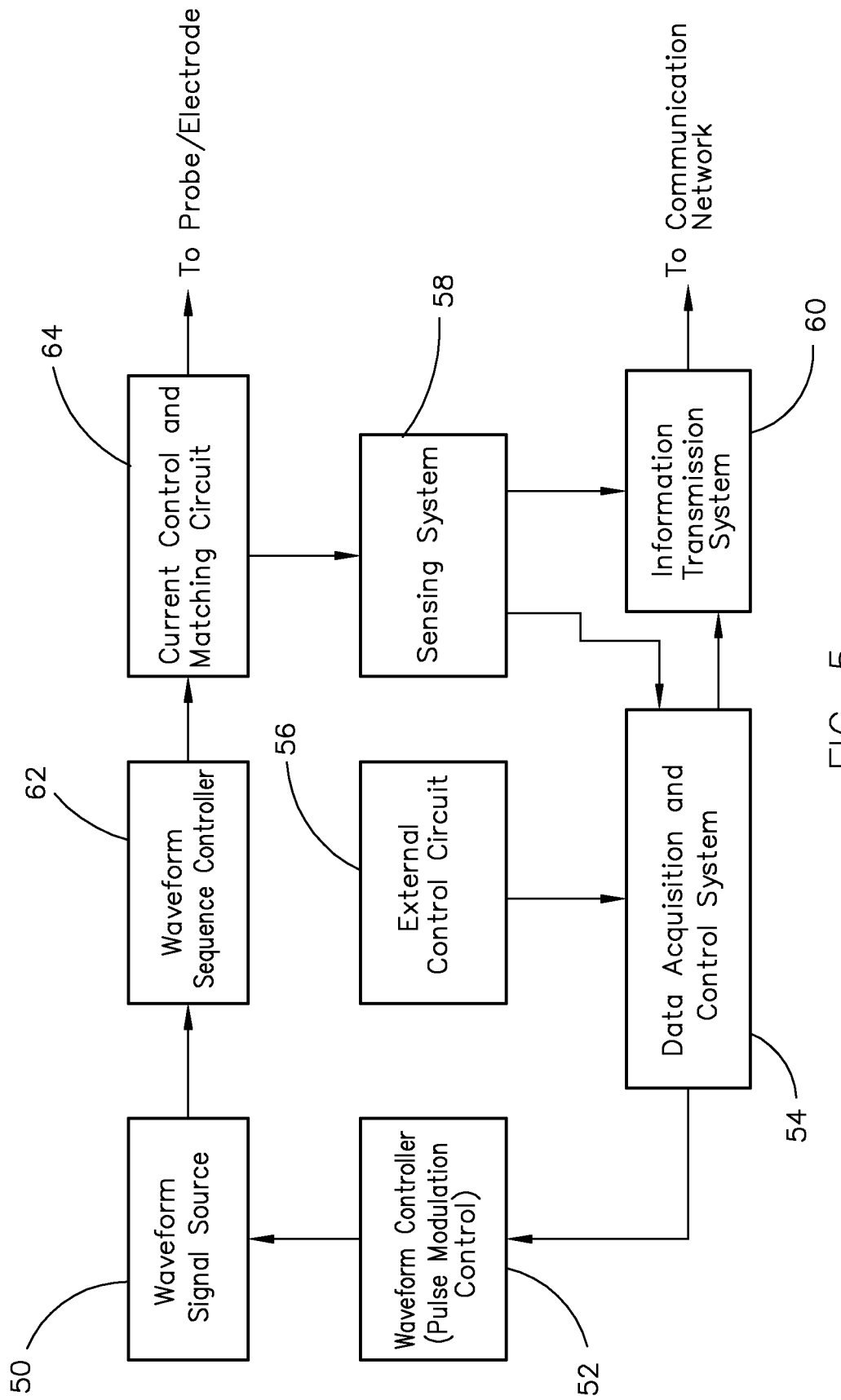
FIG. 5 is a block diagram of the signal generator circuit for the electrotherapeutic device of FIGS. 1A and 1B.

Referring now to FIG. 5, a block circuit diagram of an exemplary circuit for signal generator 12 will now be described. The circuit includes a waveform signal source 50 that is digitally controlled by a waveform controller 52. In the exemplary embodiment, waveform signal source 50 comprises a frequency variable oscillator that provides a basic pulsed current output. Of course, one skilled in the art will appreciate that waveform signal source 50 may comprise any suitable signal source known in the art.

In the exemplary embodiment, waveform controller 52 comprises a microcontroller or microprocessor that is programmed to provide an output with the appropriate waveform parameters so as to digitally control waveform signal source 50 in accordance with a protocol for treating a visual disease. The waveform parameters that may be controlled by waveform controller 52 include the pulse width, pulse period (which determines the frequency), pulse position within a pulse period, pulse coding (if any), peak current amplitude, duty cycle, and pulse shape of the pulsed current output from waveform signal source 50 (the polarity may be controlled by waveform sequence controller 62, discussed below). As discussed above, any one or combination of these waveform parameters may be varied by waveform controller 52 to generate different combinations of pulse sequences in accordance with the present invention. Thus, using different pulse modulation techniques (PWM, PPM, PFM, PCM, PAM, etc.), waveform controller 52 is capable of automatically adjusting the modulation format of the pulsed current provided by waveform signal source 50 to ensure that an appropriate set of waveform parameters is provided. It should be understood that the appropriate set of waveform parameters (i.e., the protocol for treating a visual disease) may vary between different visual diseases, may vary from patient to patient for the same visual disease, and may even vary over time for the same patient and the same visual disease, as discussed below.

It should be noted that waveform controller 52 is able to digitally control waveform signal source 50 so that the output has both large and small variations in the waveform parameters that are varied or modulated. This enables signal generator 12 to provide spectral characteristics in a waveform that are not provided in the waveforms generated by previous electrotherapeutic devices. For example, incremental frequency changes can be made so as to deliver various levels of frequency content (spectral output) in a waveform, as discussed above.

It is also possible to employ certain types of pulse modulation techniques that automatically cause the occurrence of other types of pulse modulation techniques. For example, when pulse frequency modulation (PFM) and pulse position modulation (PPM) are employed, pulse width modulation (PWM) starts to occur automatically as the duty cycle approaches 50% (depending upon the frequency range to be sequenced). If pulse width modulation (PWM) is not desired, then one can simply reduce the frequency range and/or the duty cycle. This approach also provides a way to maintain a constant peak current waveform while varying the average current levels.

Referring still to FIG. 5, the circuit also includes a data acquisition and control system 54 that receives data from an external control circuit 56 and a sensing system 58. The data received from external control circuit 56 comprises external control settings that have been input by the device manufacturer or by an operator of the device (via software or firmware) to set the operating parameters for a particular treatment protocol. For example, certain external control settings may be input via the control features provided on the front panel of signal generator 12, as shown in FIG. 1A, such as the menu system provided by buttons 30, 32 and 34 and current control dial 36. The data received from sensing system 58 comprises samples of the output current levels provided by current control and matching circuit 64. Sensing system 58 sends these samples (in the form of analog and/or digital signals) to both to the data acquisition and control system 54 for information collection and device control purposes (i.e., the information is ultimately provided to waveform controller 52) and to the information transmission system 60 for monitoring and verification purposes, as discussed below.

During a treatment, data acquisition and control system 54 monitors a variety of treatment parameters including the output current levels, treatment times, and number of treatments. Certain treatment parameters may be displayed on the device to enable the operator (e.g., health care practitioner) to maintain prescription control of the number of treatments and treatment dose. For example, in the exemplary embodiment, display 40 on the front panel of signal generator 12, as shown in FIG. 1A, provides a treatment duration indicator and a current level indicator. Data acquisition and control system 54 also provides control information to waveform controller 52, which then uses this information to control the waveform parameters of the pulsed current provided by waveform signal source 50 as discussed above.

Preferably, data acquisition and control system 54 also records various types of data for different patients and transmits such data to an information transmission system 60, which allows the information to be downloaded at the clinic or transmitted via a wired or wireless communication network (e.g., the Internet cloud) to a remote server or other network device for monitoring and analysis. In this manner, a doctor or practitioner can analyze data concerning variations in current levels and other waveform parameters for a particular patient or between patients and for different visual diseases and disease states. The doctor or practitioner can then use this data to track therapy progress for a particular patient, develop better therapy procedures for different visual diseases, and monitor variabilities in treatment points.

Referring still to FIG. 5, the circuit also includes a waveform sequence controller 62 that controls the polarity of the pulse sequences provided by waveform signal source 50. In the exemplary embodiment, a timer provides a signal to waveform sequence controller 62 to reverse the polarity of the pulse sequences as required. This enables the provision of a bipolar waveform, such as the exemplary waveforms shown in FIGS. 3A, 3B and 4B.

The output from waveform sequence controller 62 is provided to a current control and matching circuit 64 that compensates for the large variations in load impedance that can occur with different patients, different tissue properties, and different tissue hydration states. This circuit is provided at the device output to maintain safe current levels to the delicate tissues on or near a closed eyelid of a patient. In the exemplary embodiment, the output current levels are limited to 200 microamps or below.

Preferably, current control and matching circuit 64 holds the output current levels constant during treatment so that the current does not vary by more than ±10% for load impedance variations ranging from 5,000 ohms to 70,000 ohms (which is the total load from the interface between the probe and counter electrode and the tissue). For example, FIG. 6 shows the output current levels in relation to a range of load impedances in accordance with the exemplary embodiment. As can be seen, the peak output current stays relatively constant at approximately 200 microamps for load impedances in the range of 5,000 ohms to about 68,000 ohms, and then drops off by approximately 18% at 80,000 ohms. This relatively constant current control is desired for patient comfort and safety.

Finally, as discussed above, test connection 42 (see FIG. 1B) can be used to monitor the device output with an oscilloscope, spectrum analyzer, waveform analyzer, or other kinds of test equipment. Preferably, an isolation circuit is provided between the current control and matching circuit 64 and test connection 42 in order to prevent the test equipment from interfering with the output waveform and output current levels.

Method of Operation

In operation, an electrotherapeutic device in accordance with the present invention (such as electrotherapeutic device 10 described above) is used to provide microcurrent stimulation therapy to treat patients suffering from a variety of different visual diseases. Examples of visual diseases that may be treated include macular degeneration, diabetic retinopathy, diabetic macular edema, retinitis pigmentosa, primary open angle glaucoma, stargardt's disease, optic nerve conditions (e.g., anterior ischemic optic neuropathy, hereditary autosomal dominant optic atrophy, optic neuritis and neuropathy associated with MS, pseudo tumor cerebri, optic atrophy), ischemic macula edema and other ischemic retinal conditions, retinal artery occusion, retinal vein occlusion, retinal detachment, corneal edema and other corneal problems including herpes zoster ophthalmicus, ocular trauma, blepharospasm, visual field loss after stroke, bell's palsy, and amaurosis. Of course, it should be understood that this list is not exhaustive and that other visual diseases may also be treated in accordance with the present invention.

In an exemplary method, electrotherapeutic device 10 is used to deliver a waveform (as described above) to one or more stimulation points within an eye region of a patient. A closed circuit is created when stimulation probe 14 is placed in contact with each stimulation point and counter electrode 16 is attached to the patient's right temple or other part of the body. The waveform generated by signal generator 12 travels from probe 14 through the patient's body to counter electrode 16 and back to signal generator 12. Of course, it should be understood that electrotherapeutic device 10 is just an exemplary device and that other devices may be used to perform the method of the present invention.

The eye region of the patient within which the stimulation points are located preferably comprises a region that includes the eye and tissue within 15 centimeters of the eye, and typically tissue within 5 centimeters of the eye. In most cases, each stimulation point is located on or near a closed eyelid of the patient within the eye region. When stimulating the closed eyelid, the patient preferably looks away from the probe with eyes closed, which moves the macula closer to the region of maximum stimulation.

In one example, four stimulation points are provided on the upper eyelid and four stimulation points are provided on the lower eyelid for a total of eight stimulation points within the eye region. FIG. 7 illustrates the eight stimulation points which are stimulated and the preferred order of stimulation. The stimulation preferably occurs in the order from point one to point eight. In this example, the probe is held at each stimulation point for about 40 seconds to thereby complete one treatment.

In another example, there are two stimulation points on the upper eyelid and two stimulation points on the lower eyelid for a total of four stimulation points within the eye region. The stimulation points on the upper eyelid are preferably stimulated before the stimulation points on the lower eyelid. In this example, the probe is held at each stimulation point for about 40 seconds to thereby complete one treatment.

The number and frequency of treatments will vary significantly between patients, depending upon the visual disease to be treated, the severity of the damage done to the retinal tissue with disease progression, the patient's age, the date of first diagnosis, the patient's health, the patient's lifestyle, the environment and other factors. For example, in some cases, a single treatment per day may be sufficient, while in other cases it may be necessary to provide 2 to 8 treatments or more per day. Also, in some cases, treatments may be provided on three days over a one week period, while in other cases it may be necessary to provide treatments every day over a one or two week period or more. Thus, the preferred treatment protocol will vary from patient to patient and may even vary over time for the same patient.

It should also be understood that the waveform delivered to each stimulation point during each treatment will depend upon the visual disease to be treated and the disease state. As discussed above, each visual disease responds to a specific combination of pulse modulation techniques and associated waveform parameters, which are therapeutically efficacious for the specific condition being treated and the specific biochemical events, processes, and mechanisms-of-action to be influenced. For example, it is believed that a hybrid waveform architecture in which three or more waveform parameters are modulated or varied is a preferred approach for microcurrent stimulation therapy in many visual disease applications. Further, different patients may possess slightly different electrotherapeutic response parameters for the same visual disease. For example, the waveform parameters that one patient responds to during electrotherapy may not be exactly the same as the waveform parameters that are optimum for other patients. In fact, the same patient may respond to slightly different waveform parameters with time, aging, physical condition, hormone levels, the use of other medical treatments or therapies and environment. Thus, any one of the waveform parameters described above or any combination of these waveform parameters may be modulated or varied in accordance with a protocol for treating a visual disease.

The effectiveness of an electrotherapeutic treatment can be determined immediately after the treatment has been completed by the use of visual acuity testing with eye charts, as well as a number of non-invasive optical diagnostic tools utilized in ophthalmology and optometry, such as a near infrared line scanning laser ophthalmoscope and/or various forms of optical coherence tomography. These tests may also be used to make adjustments in the treatment parameters in order to enhance the therapeutic response. For some conditions, the effects of electrotherapeutic treatment of the retina can be detected and observed in less than an hour, whereas other treatment modalities may not show an effect for weeks.

While the present invention has been described and illustrated hereinabove with reference to several exemplary embodiments, it should be understood that various modifications could be made to these embodiments without departing from the scope of the invention. Therefore, the present invention is not to be limited to the specific device configuration, waveforms, or methodologies of the exemplary embodiments, except insofar as such limitations are included in the following claims.

What is claimed and desired to be secured by Letters Patent is as follows:

1. An electrotherapeutic device for treating a visual disease using microcurrent stimulation, comprising:
    a signal generator comprising (a) a waveform signal source configured to provide a waveform comprising a series of current pulses having a peak current amplitude between 1 microamp and 450 microamps and (b) a waveform controller connected to the waveform signal source and programmed to generate a digital control signal that determines a plurality of waveform parameters for the waveform in accordance with a visual disease treatment protocol, wherein one of the waveform parameters comprises a frequency that is selectively varied to cause the waveform signal source to provide the current pulses at a plurality of varying frequencies within a defined frequency range, wherein another one of the waveform parameters comprises a pulse width that is selectively varied to cause the waveform signal source to provide the current pulses at a plurality of varying pulse widths, and wherein the waveform signal source is configured to receive the digital control signal and provide the waveform so that the frequency and the pulse width of the current pulses are varied simultaneously within the waveform during a treatment session; and
    an applicator connected to the signal generator and including an electrode configured to receive and apply the waveform within an eye region during the treatment session.

2. The electrotherapeutic device of claim 1, wherein the defined frequency range is 0.3 Hz to 300 Hz.

3. The electrotherapeutic device of claim 2, wherein the current pulses are provided at 75% or more of the discrete frequencies within the defined frequency range.

4. The electrotherapeutic device of claim 2, wherein the current pulses are provided at 90% or more of the discrete frequencies within the defined frequency range.

5. The electrotherapeutic device of claim 1, wherein the defined frequency range is 0.1 Hz to 50 Hz.

6. The electrotherapeutic device of claim 5, wherein the current pulses are provided at 75% or more of the discrete frequencies within the defined frequency range.

7. The electrotherapeutic device of claim 5, wherein the current pulses are provided at 90% or more of the discrete frequencies within the defined frequency range.

8. The electrotherapeutic device of claim 1, wherein the defined frequency range is 0.05 Hz to 10 Hz.

9. The electrotherapeutic device of claim 8, wherein the current pulses are provided at 75% or more of the discrete frequencies within the defined frequency range.

10. The electrotherapeutic device of claim 8, wherein the current pulses are provided at 90% or more of the discrete frequencies within the defined frequency range.

11. The electrotherapeutic device of claim 1, wherein another one of the varied waveform parameters comprises one of peak current amplitude, duty cycle, and pulse shape.

12. The electrotherapeutic device of claim 11, wherein the waveform comprises a first pulse sequence and a second pulse sequence.

13. The electrotherapeutic device of claim 12, wherein the signal generator further comprises a waveform sequence controller that varies a polarity of each of the first and second pulse sequences is varied to generate a bipolar waveform.

14. The electrotherapeutic device of claim 13, wherein the varied waveform parameters of the first pulse sequence are the same as the varied waveform parameters of the second pulse sequence.

15. The electrotherapeutic device of claim 13, wherein the varied waveform parameters of the first pulse sequence are different than the varied waveform parameters of the second pulse sequence.

16. The electrotherapeutic device of claim 1, wherein the visual disease comprises macular degeneration.

17. The electrotherapeutic device of claim 1, wherein the applicator comprises a probe configured to apply the waveform to the stimulation point and a counter electrode configured for attachment to a body part.

18. The electrotherapeutic device of claim 1, wherein the current pulses have a peak current amplitude between 1 microamp and 450 microamps.

19. The electrotherapeutic device of claim 1, wherein the current pulses have a peak current amplitude between 180 microamps and 220 microamps.

20. The electrotherapeutic device of claim 1, wherein the waveform has an average current between 70 microamps and 200 microamps.

21. The electrotherapeutic device of claim 1, wherein the waveform has an average current between 90 microamps and 100 microamps.

* * * * *